United States Patent
Takeishi

(10) Patent No.: US 9,972,192 B2
(45) Date of Patent: May 15, 2018

(54) ACTIVITY INFORMATION MEASURING APPARATUS, AND METHOD AND PROGRAM FOR ASSISTING PREVENTION OF FORGOTTEN ATTACHMENT OF THE SAME

(71) Applicant: OMRON HEALTHCARE CO., LTD., Muko-shi, Kyoto (JP)

(72) Inventor: Naoki Takeishi, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 0 days. days.

(21) Appl. No.: 15/387,698

(22) Filed: Dec. 22, 2016

(65) Prior Publication Data

US 2017/0098365 A1 Apr. 6, 2017

Related U.S. Application Data

(63) Continuation of application No. PCT/JP2015/068498, filed on Jun. 26, 2015.

(30) Foreign Application Priority Data

Jun. 26, 2014 (JP) ................................. 2014-131399

(51) Int. Cl.
*G08B 23/00* (2006.01)
*G08B 21/24* (2006.01)
(Continued)

(52) U.S. Cl.
CPC .......... *G08B 21/24* (2013.01); *A63B 24/0062* (2013.01); *G08B 21/06* (2013.01);
(Continued)

(58) Field of Classification Search
CPC .......... G08B 21/24; G08B 21/06; G08B 6/00; G08B 5/36; G08B 3/10; A63B 24/0062;
(Continued)

(56) References Cited

U.S. PATENT DOCUMENTS

2011/0018720 A1* 1/2011 Rai ........................ A61B 5/048
340/575
2011/0267196 A1* 11/2011 Hu ........................ A61B 5/0002
340/575
(Continued)

FOREIGN PATENT DOCUMENTS

JP 11-178798 A 7/1999
JP 2000-321092 A 11/2000
(Continued)

OTHER PUBLICATIONS

Official Communication issued in International Patent Application No. PCT/JP2015/068498, dated Sep. 29, 2015.

*Primary Examiner* — Anh V La
(74) *Attorney, Agent, or Firm* — Keating and Bennett, LLP

(57) ABSTRACT

An activity information measuring apparatus includes a detector that detects information corresponding to motion of a user. The activity information measuring apparatus analyzes the user's activity based on information detected by the detector, detects, based on the analysis results, a timing at which the user stopped sleeping and started moving, and makes an announcement to the user by operating an announcer in synchronization with the detected timing.

6 Claims, 5 Drawing Sheets

(51) Int. Cl.
*A63B 24/00* (2006.01)
*G08B 21/06* (2006.01)
*G08B 3/10* (2006.01)
*G08B 5/36* (2006.01)
*G08B 6/00* (2006.01)

(52) U.S. Cl.
CPC ....... *A63B 2220/17* (2013.01); *A63B 2220/40* (2013.01); *A63B 2220/73* (2013.01); *A63B 2220/74* (2013.01); *G08B 3/10* (2013.01); *G08B 5/36* (2013.01); *G08B 6/00* (2013.01)

(58) Field of Classification Search
CPC ............ A63B 2220/17; A63B 2220/74; A63B 2220/40; A63B 2220/73
USPC ................. 340/457, 573.1, 575, 540, 539.12
See application file for complete search history.

(56) References Cited

U.S. PATENT DOCUMENTS

| | | | | |
|---|---|---|---|---|
| 2012/0092171 A1* | 4/2012 | Hwang | ................. | G06F 19/345 340/575 |
| 2013/0154838 A1* | 6/2013 | Alameh | ............... | G04G 13/023 340/575 |

FOREIGN PATENT DOCUMENTS

| | | | |
|---|---|---|---|
| JP | 2010-264193 | A | 11/2010 |
| JP | 2015-16193 | A | 1/2015 |
| WO | 2010/082667 | A1 | 7/2010 |
| WO | 2013/042631 | A1 | 3/2013 |

\* cited by examiner

ACTIVITY INFORMATION MEASURING APPARATUS, AND METHOD AND PROGRAM FOR ASSISTING PREVENTION OF FORGOTTEN ATTACHMENT OF THE SAME

CROSS REFERENCE TO RELATED APPLICATIONS

This application claims the benefit of priority to Japanese Patent Application No. 2014-131399, filed Jun. 26, 2014 and is a Continuation Application of PCT/JP2015/068498 filed on Jun. 26, 2015. The entire contents of each application are hereby incorporated by reference.

BACKGROUND OF THE INVENTION

1. Field of the Invention

The present invention relates to an activity information measuring apparatus, and a method and a program, for assisting prevention of forgotten attachment of the same.

2. Description of the Related Art

Recent years have seen the active development of apparatuses that are able to identify a person's activities (walking, running, ascending/descending stairs, sleeping, etc.), measure an activity level (movement amount, number of steps, walking distance, consumed calories, etc.)/and so on, using motion detection sensors that detect body motion, such as acceleration sensors and angular velocity sensors. In this specification, information regarding the type of activity and the activity level is collectively referred to as activity information.

This type of apparatus promotes a desire in the user to control their health by presenting the user with activity information, and is desirably used continuously every day. However, it is difficult to remember to use the apparatus every day, and the user may eventually forget to use it. If the user continues to forget to use the apparatus, there is concern that the apparatus will no longer be used at all.

JP 2000-321092A discloses a pedometer that prevents forgotten attachment thereof by making an announcement through sounding a buzzer if walking has not been detected for a certain period of time since walking was last detected.

JP H11-178798A discloses a healthcare device that prevents the user from forgetting to use it by prompting use through sounding a buzzer when a set time comes.

WO 2010/082667 is not related to forgotten attachment prevention, but discloses a pedometer that outputs a melody during operation in a mode for measuring step count data during logging in order to inform the user that the pedometer is operating in that mode.

The pedometer disclosed in JP 2000-321092A prevents the user from forgetting to attach it by making an announcement to the user if walking has not been detected for a while, but if the user is away from home while the announcement is being made, the user cannot realize that they have forgotten to attach the pedometer.

The healthcare device disclosed in JP H11-178798A makes an announcement when a set time comes, and therefore if the user is away from home while the announcement is being made, the user cannot realize that they have forgotten to use the healthcare device.

The pedometer disclosed in WO 2010/082667 does not give consideration to forgotten attachment prevention.

SUMMARY OF THE INVENTION

Preferred embodiments of the present invention provide an activity information measuring apparatus that contributes to health improvement by preventing forgotten attachment thereof, and a method and a program for assisting prevention of forgotten attachment of the same.

An activity information measuring apparatus according to a preferred embodiment of the present invention includes: a detector that detects information corresponding to motion of a user; a sleeping state determiner that determines whether or not the user is in a sleeping state; a timing detector that, based on information detected by the detector, determines a timing at which the user started to move after the sleeping state determiner determined that the user is in the sleeping state; and an announcer that makes an announcement to the user in synchronization with the timing.

A method for assisting prevention of forgotten attachment of an activity information measuring apparatus according to another preferred embodiment of the present invention includes: a step in which the activity information measuring apparatus, which includes a detector that detects information corresponding to motion of a user, detects whether or not the user is in a sleeping state; a step in which after detection that the user is in the sleeping state, the activity information measuring apparatus detects, based on information detected by the detector, a timing at which the user started to move; and a step in which the activity information measuring apparatus makes an announcement to the user in synchronization with the detected timing.

A non-transitory computer readable medium includes a program for assisting prevention of forgotten attachment of an activity information measuring apparatus according to another preferred embodiment of the present invention, wherein the program causes a computer to execute the steps of the above-described method for assisting prevention of forgotten attachment.

According to various preferred embodiments of the present invention, it is possible to provide an activity information measuring apparatus that contributes to health improvement by preventing forgotten attachment thereof, and a method and a program for assisting prevention of forgotten attachment of the same.

The above and other elements, features, steps, characteristics and advantages of the present invention will become more apparent from the following detailed description of the preferred embodiments with reference to the attached drawings.

DETAILED DESCRIPTION OF THE PREFERRED EMBODIMENTS

Hereinafter, preferred embodiments of the present invention will be described with reference to the drawings.

Figure 1:
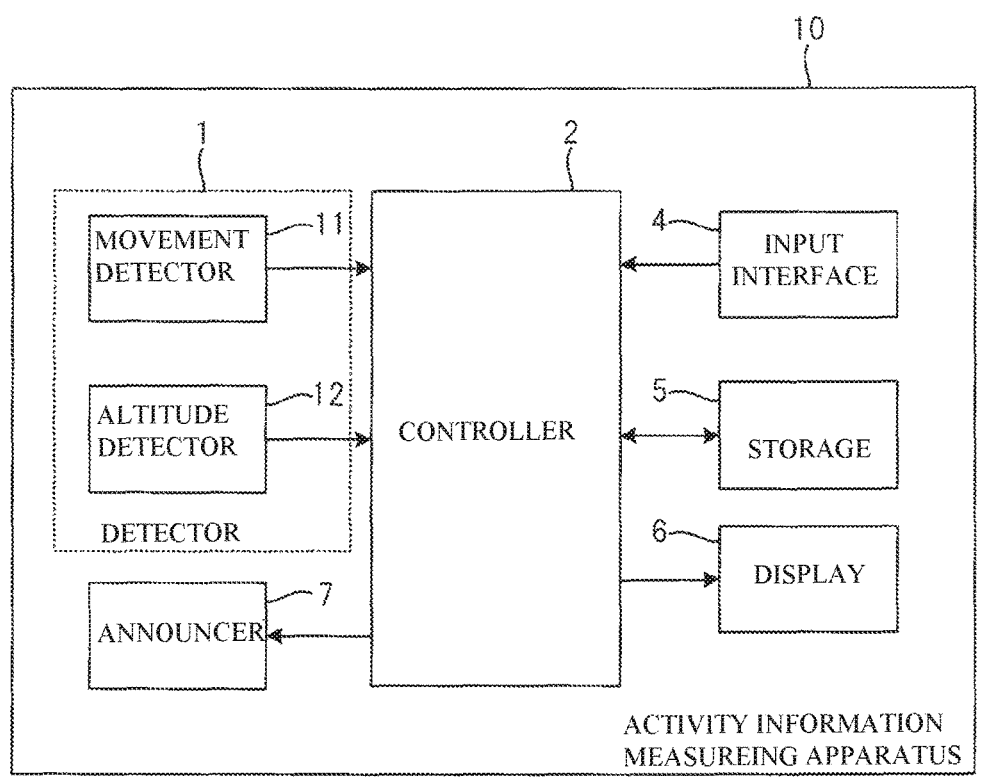
FIG. 1 is a block diagram, showing a schematic configuration of an activity information measuring apparatus 10 for describing a preferred embodiment of the present invention.

FIG. 1 is a block diagram showing the schematic configuration of an activity information measuring apparatus 10 for describing a preferred embodiment of the present invention.

The activity information measuring apparatus 10 is attached to a user's body for use.

The activity information measuring apparatus 10 includes a detector 1, a controller 2 that performs overall control, an input interface 4, a storage 5 that includes a storage medium such as a flash memory or a ROM (Read Only Memory), a display 6 that displays various types of information, and an announcer 7.

The detector 1 detects information corresponding to motion of the user's body to which the activity information measuring apparatus 10 is attached, and includes a movement detector 11 and an altitude detector 12.

The movement detector 11 detects motion (acceleration, angular velocity, etc.) of the user's body to which the activity information measuring apparatus 10 is attached, and includes various sensors such as an acceleration sensor and an angular velocity sensor, and a signal processor that processes signals output by the various sensors. It is sufficient that the movement detector 11 includes at least one sensor and a signal processor that processes signals from, that sensor.

The altitude detector 12 includes an atmospheric pressure sensor, and detects the altitude of the portion to which the activity information measuring apparatus 10 is attached by processing a detection signal from the atmospheric pressure sensor. Note that the altitude detector 12 may be omitted. The altitude of the portion to which the activity information measuring apparatus 10 is attached changes depending on the user's activity (e.g., ascending/descending stairs). Accordingly, this altitude information is also information corresponding to motion of the portion to which the activity information measuring apparatus 10 is attached.

The controller 2 preferably is mainly constituted by a processor that executes programs stored in the ROM of the storage 5.

The input interface 4 is a device used to input various instructions to the controller 2, and may include buttons, a touch panel installed on the display 6, or the like.

The storage 5 stores information detected by the detector 1, and stores information necessary for operation of the activity information measuring apparatus 10.

The announcer 7 makes an announcement to the user using sound, light, vibration, or the like, and may preferably be a device such as a speaker, an LED (Light Emitting Diode), a vibrator, or the like.

Figure 2:
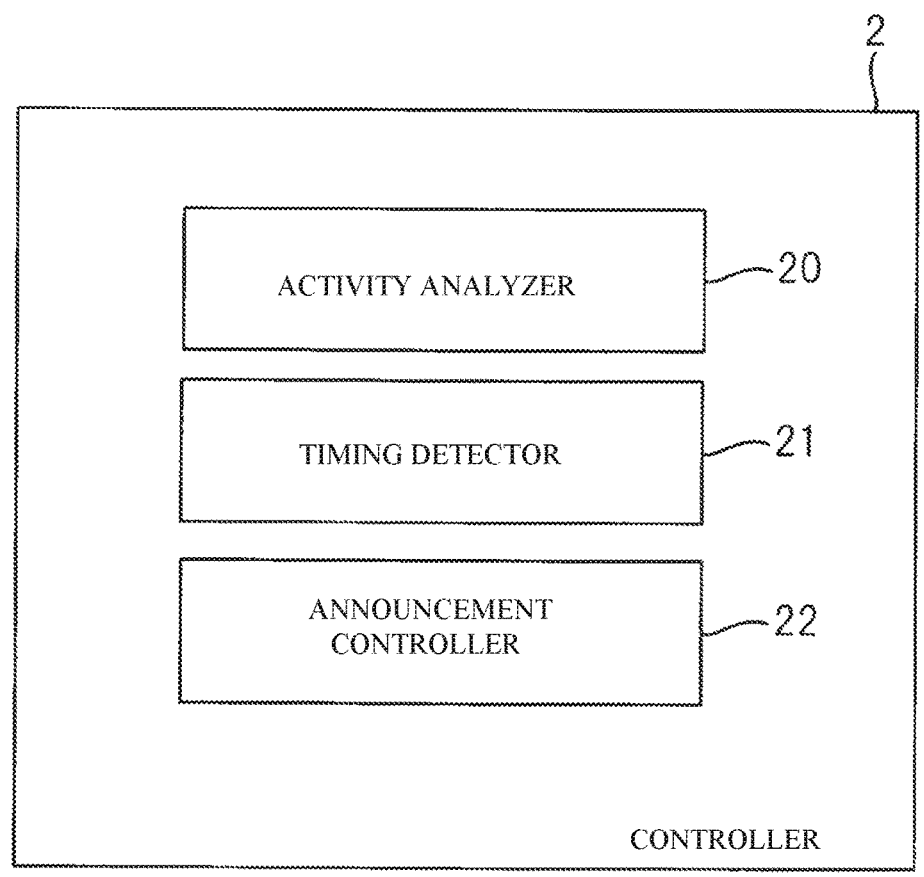
FIG. 2 is a functional block diagram of a controller 2 in the activity information measuring apparatus 10 shown in FIG. 1.

FIG. 2 is a diagram showing functional blocks of the controller 2 including a processor that is configured or programmed to execute a program stored in the storage 5 of the activity information measuring apparatus 10 shown in FIG. 1.

As shown in FIG. 2, the controller 2 is configured or programmed to include an activity analyzer, a timing detector 21, and an announcement controller 22.

The activity analyzer 20 analyzes the user's activity based on information detected by the detector 1, and stores activity information obtained through the analysis (analysis results) in the storage 5. This activity information includes information indicating the type of activity (sleeping, moving, eating, etc.) performed by the user to which the activity information measuring apparatus 10 is attached, and the activity level of the user (movement amount, number of steps, etc.).

Based on the information detected by the detector 1, the activity analyzer 20 performs activity analysis to determine whether or not the user is in a sleeping state. The activity analyzer 20 is configured or programmed to function as a sleeping state determiner that determines whether or not the user is in a sleeping state based on the information detected by the detector 1.

Whether or not the user is in the sleeping state is able to be detected based on the acceleration and indicators calculated based on the acceleration (bed turnover angle, body orientation, movement amount, etc.) in the information detected by the detector 1. A sleeping state detection method is disclosed in JP 2005-124858A, for example.

The timing detector 21 detects the timing at which movement started after it was determined that the user is in the sleeping state (referred to hereinafter as the activity start timing), based on information detected by the detector 1.

The timing detector 21 obtains a value indicating the activity level in the user's sleeping period (a period for which it was determined that the user is in the sleeping state) that is generated by the activity analyzer 20 (e.g., a representative value indicated by the average value or the like of the activity level in a certain period during the sleeping period), then compares this obtained value (referred to as a first activity level) with the most recent activity level generated by the activity analyzer 20 (referred to as the second activity level), and determines that the user has stopped sleeping and started moving if the second activity level has changed to a value that is larger than the first activity level by an amount greater than or equal to a threshold value.

The announcement controller 22 makes an announcement to the user by operating the announcer 7 in synchronization with the activity start timing detected by the timing detector 21. Preferably, the announcement is made by outputting an electronic melody, a voice message such as "Let's do our best today too", or the like, or operating the vibrator.

The following describes operations of the activity information measuring apparatus 10 having the configuration described above.

Figure 3:
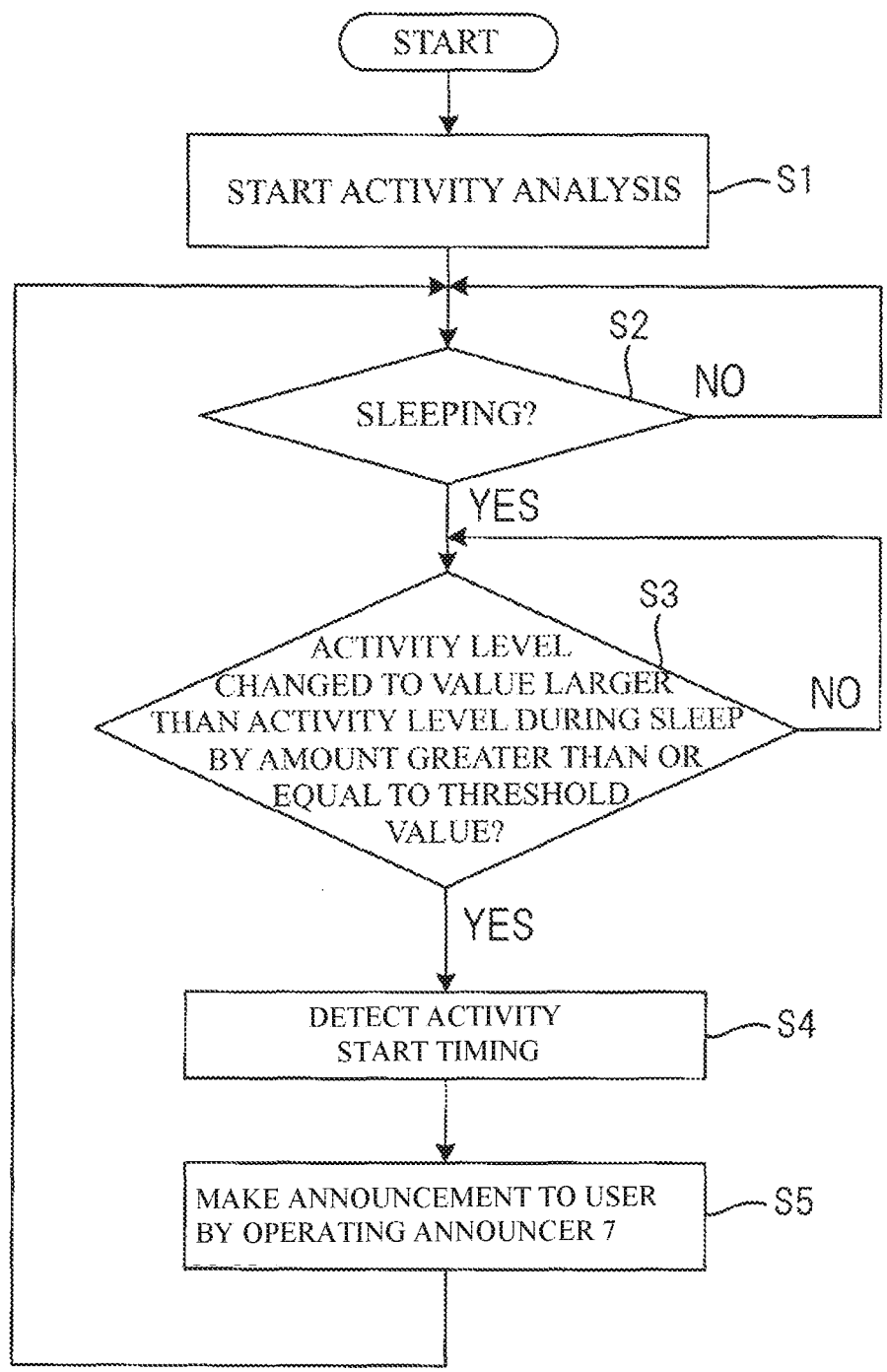
FIG. 3 is a flowchart for describing operations of the activity information measuring apparatus 10.

FIG. 3 is a flowchart for describing operations of the activity information measuring apparatus 10.

When the power is turned on, the detector 1 starts to detect information, the controller 2 starts to perform activity analysis based on the detected information, and activity information obtained as a result of the analysis is successively stored to the storage 5 (step S1).

The controller 2 determines whether or not the user is sleeping based on the activity information stored in the storage 5 (step S2), and then performs the processing of step S3 if the user is sleeping.

In step S3, the controller 2 compares the most recent activity level that was generated based on the information detected by the detector 1 and the average value of the activity level of the user in a certain period during the sleeping period. If the most recent activity level has changed to a value larger than the average value by an amount greater than or equal to the threshold value (step S3: YES), the controller 2 determines that the user has stopped sleeping and started moving, and detects the activity start timing (step S4).

After step S4, the controller 2 makes an announcement to the user by operating the announcer 7 (step S5), and then returns to the processing of step S2.

As described above, according to the activity information measuring apparatus 10, an announcement is made by the announcer 7 at the timing when the user wearing the activity information measuring apparatus 10 has woken from sleep and started moving. In other words, if the user is wearing the activity information measuring apparatus 10, an announcement is always made at the timing when activity starts for the day. Accordingly, the user becomes accustomed to the announcement from the activity information measuring apparatus 10, and will be able to realize that they have forgotten to attach it if there is no announcement after waking up and starting to move.

The activity information measuring apparatus 10 detects the activity start timing based on the end of the user's sleeping period, and therefore is able to accurately detect the start of the user's activity for the day. Also, according to the activity information measuring apparatus 10, by setting the threshold value set in step S3 to a large value, it is possible to prevent an announcement from being made when the activity level increases due to rolling over in bed or the like, and the burden on the user is able to be alleviated. Also, the announcement is able to be automatically made in accordance with the user's activity pattern, without the user needing to perform any special operations, thus making it possible to alleviate the burden on the user.

Note that the activity analyzer 20 is able to determine whether or not the user is in the sleeping state even if the activity information measuring apparatus 10 is not attached to the user's body. For example, if the activity information measuring apparatus 10 is placed next to the user's pillow, whether or not the user is in the sleeping state is able to be determined by the movement detector 11 detecting user movement via movement of the bedding. In this case, the user puts on the activity information measuring apparatus 10 after waking up, and the announcer 7 makes an announcement when movement starts in this state.

Figure 4:
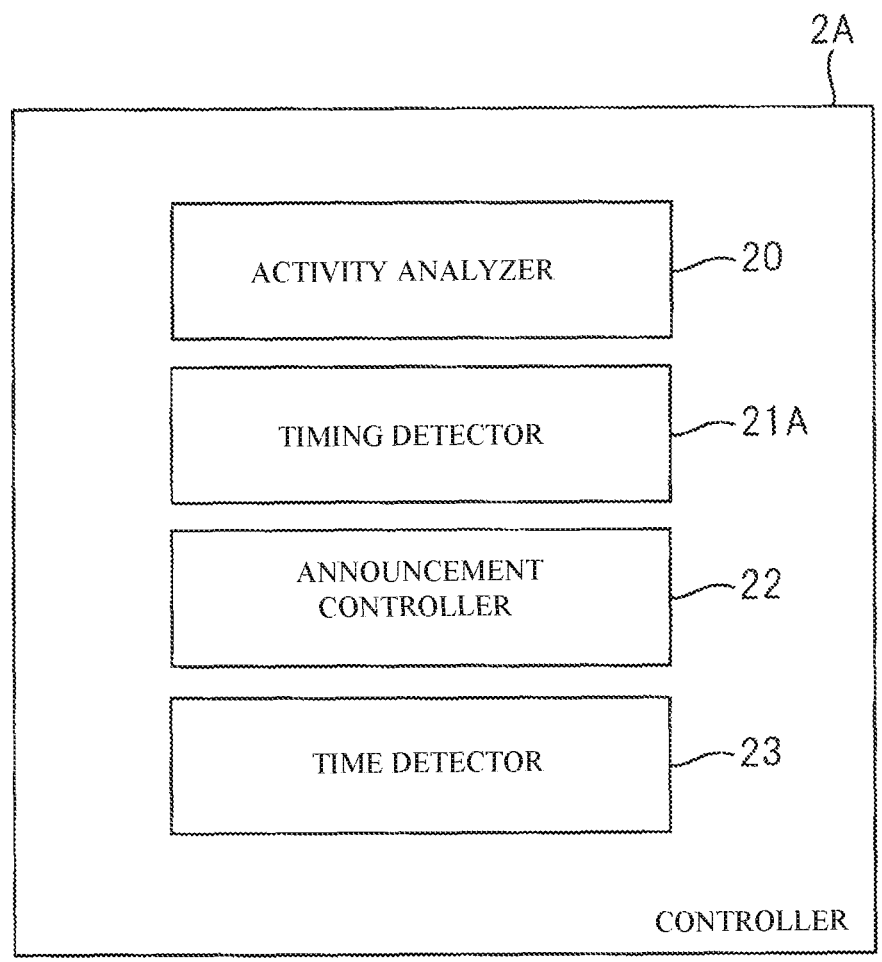
FIG. 4 is a functional block diagram of a controller 2A that is a modified example of the controller 2 in the activity information measuring apparatus 10 shown in FIG. 1.

FIG. 4 is a functional block diagram of a controller 2A that is a modified example of the controller 2 in the activity information measuring apparatus 10 shown in FIG. 1.

The controller 2A preferably has the same configuration as the controller 2, with the exception that the timing detector 21 has been replaced with a timing detector 21A, and a time determiner 23 has been added. The functional blocks of the controller 2A are configured or programmed by the execution of a program stored in the ROM of the storage 5.

The timing detector 21A compares the first activity level and the second activity level similarly to the timing detector 21. If the second activity level is larger than the first activity level by an amount greater than or equal to the threshold value, and the time at which the change occurred is at or after a specified time, it is determined that the user stopped sleeping and started moving.

The time determiner 23 determines the specified time based on a history of the times at the activity start timing detected by the timing detector 21A, that is to say a history of user wakeup times.

For example, the time determiner 23 calculates an average time of the morning wakeup times over a certain period in the past for the user, and sets this average time as the specified time.

Note that if the activity start timing has not been detected multiple times by the timing detector 21A, a predetermined value (e.g., 7:00 am) may be set as the specified time, and then the specified time may be updated by the time determiner 23 after the activity start timing has been detected multiple times.

Figure 5:
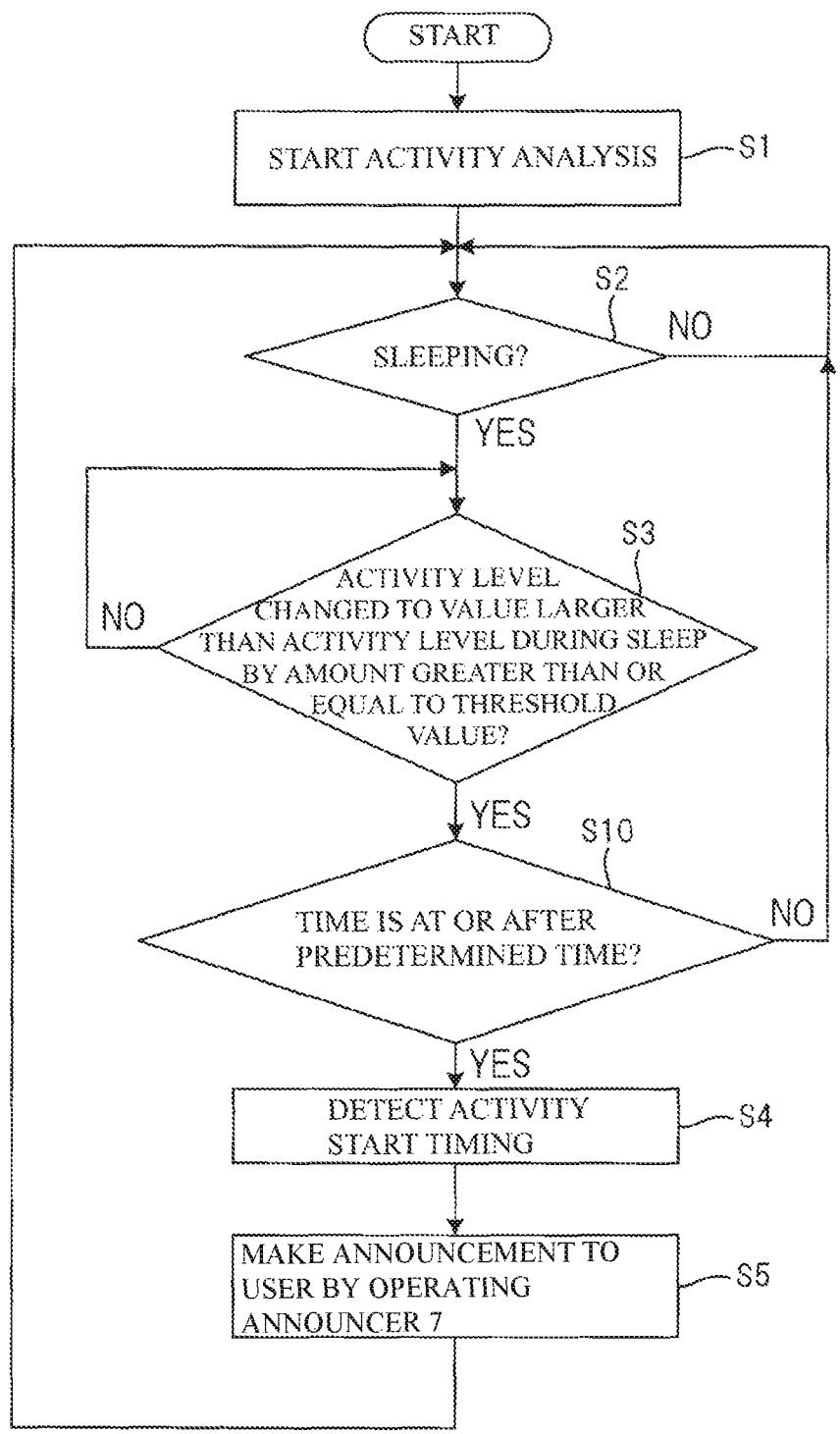
FIG. 5 is a flowchart for describing operations of the activity information measuring apparatus 10 in which the controller 2 is replaced with the controller 2A.

FIG. 5 is a flowchart for describing operations of the activity information measuring apparatus 10 in which the controller 2 is replaced with the controller 2A. Processing in FIG. 5 that is the same as in FIG. 3 is denoted by the same reference signs and will not be described.

If the result of the determination in step S3 is YES, the controller 2A compares the time at which the determination was made with the specified time, and, if the time of the affirmative determination in step S3 is at or after the specified time (step S10: YES), the controller 2A performs the processing of step S4 and onward. If the time of the affirmative determination in step S3 is before the specified time (step S10: NO), the controller 2A determines that the user moved temporarily, and then returns to the processing of step S2.

As described above, according to the activity information measuring apparatus 10 in which the controller 2 is replaced with the controller 2A, if the user wearing the activity information measuring apparatus 10 starts to move temporarily while in bed, for example if the user goes to the bathroom at night after going to bed, the announcer 7 does not make an announcement if the time is not at or after the specified time. This therefore prevents the user from feeling displeasure. Also, by setting a morning wakeup time as the specified time, an announcement will not be made if the user takes an afternoon nap, and it is possible to make an announcement only at the activity start timing for the day.

Also, according to the activity information measuring apparatus 10 that includes the controller 2A, the specified time is automatically determined according to the user's waking pattern, thus making it possible to obtain an effect of preventing the making of an announcement during sleep or after an afternoon nap, without requiring the user to be aware of it.

In the foregoing description, the activity analyzer 20 determines whether or not the user is in the sleeping state based on information detected by the detector 1. However, the determination regarding the sleeping state may be made based on information from an external device.

For example, a configuration is possible in which the activity information measuring apparatus 10 is able to communicate with a sleep management apparatus that is able to indirectly detect body movement based on the movement of bedding and manage the sleeping state based on the detected body movement. The user uses the sleep management apparatus while sleeping, and either attaches the activity information measuring apparatus 10 to their body or places it on a table.

If the activity analyzer 20 of the activity information measuring apparatus 10 receives information indicating that the user is sleeping from the sleep management apparatus, it determines that the user of the activity information measuring apparatus 10 is in the sleeping state, and if it has not received information indicating that the user is sleeping from the sleep management apparatus, it determines that the user is not in the sleeping state.

In this way, by making the sleeping state determination in cooperation with the sleep management apparatus, it is possible to simplify the processing performed by the activity information measuring apparatus 10 and achieve cost reduction.

Note that if the activity information measuring apparatus 10 is configured or programmed to make the sleeping state determination based on information from the detector 1, there are cases where it is not possible to determine whether or not the user is in the sleeping state.

For example, if the activity information measuring apparatus 10 has been placed on a table, the information detected by the detector 1 will hardly change at all. It is therefore not possible to determine whether the user is sleeping or awake.

The following describes the configuration of an activity information measuring apparatus 10 that is able to handle this case where the activity analyzer 20 cannot determine whether or not the user is in the sleeping state.

The analysis results of the activity analyzer 20 are stored in the storage 5 of the activity information measuring apparatus 10. Specifically, if the activity analyzer 20 has determined that the user is in the sleeping state even a single time, the storage 5 stores data regarding the sleeping period for at least one day of the user.

If the activity analyzer 20 cannot determine whether or not the user is in the sleeping state, the timing detector 21 determines a past wakeup time of the user that is based on the data stored in the storage 5. The timing detector 21 then determines the timing at which the user started to move after the determined wakeup time according to the analysis results (e.g., magnitude of the activity level) of the activity analyzer 20, and uses the determined timing as the timing at which the user stopped sleeping and started moving.

According to this configuration, if the activity information measuring apparatus 10 is placed at a location away from the bedding, and then the user goes to bed, wakes up at the normal wakeup time, puts the activity information measuring apparatus 10 on, and then moves, an announcement will be made by the announcer 7 of the activity information measuring apparatus 10. According to this configuration, even if the user falls asleep without wearing the activity information measuring apparatus 10, it is possible to detect the timing at which the user stopped sleeping and started moving.

Preferred embodiments of the present invention can also be realized as a non-transitory computer-readable medium, including a program that, causes a computer to execute the processing steps performed by the functional blocks of the controllers 2 and 2A described above.

Examples of a non-transitory computer-readable recording medium include optical media such as a CD-ROM (Compact Disc-ROM) and magnetic recording media such as a memory card. Such a program can also be provided by being downloaded via a network.

Note that the preferred embodiments of the present invention disclosed above is to be understood as being in all ways exemplary and in no way limiting. The scope of the present invention is defined not by the aforementioned descriptions but by the scope of the appended claims, and all changes which come within the meaning and range of equivalency of the scope of the claims are intended to be included therein as well.

As described above, the present specification discloses the following matter.

The disclosed activity information measuring apparatus includes: a detector that detects information corresponding to motion of a user; a sleeping state determiner that determines whether or not the user is in a sleeping state; a timing detector that, based on information detected by the detector, determines a timing at which the user started to move after the sleeping state determiner determined that the user is in the sleeping state; and an announcer that makes an announcement to the user in synchronization with the timing.

In the disclosed activity information measuring apparatus, the sleeping state determiner may determine whether or not the user is in the sleeping state based on information detected by the detector, and the timing detector may determine that the user started to move if an activity level of the user that is based on information detected by the detector changed to a value that is larger than, by an amount greater than or equal to a threshold value, a value in a period for which it was determined that the user is in the sleeping state, and furthermore if the time at which the change occurred is at or after a specified time.

The disclosed activity information measuring apparatus may further include a time determiner that determines the specified time according to a history of times at which the timing was detected by the timing detector.

The disclosed activity information measuring apparatus may further include a storage that stores data regarding a sleeping period of the user during which it is determined that the user is in the sleeping state, wherein if the sleeping state determiner cannot determine whether or not the user is in the sleeping state, the timing detector may detect, based on information detected by the detector, a timing at which the user moved at or after a past wakeup time that is based on data stored in the storage, and use the detected timing as the timing at which the user started to move after the sleeping state ended.

A method for assisting prevention of forgotten attachment of the disclosed activity information measuring apparatus includes: a step in which the activity information measuring apparatus, which includes a detector that detects information corresponding to motion of a user, detects whether or not the user is in a sleeping state; a step in which after detection that the user is in the sleeping state, the activity information measuring apparatus detects, based on information detected by the detector, a timing at which the user started to move; and a step in which the activity information measuring apparatus makes an announcement to the user in synchronization with the detected timing.

A non-transitory computer-readable medium includes a program to assist prevention of forgotten attachment of the disclosed activity information measuring apparatus, wherein the program causes a computer to execute the steps of the method for assisting prevention of forgotten attachment.

According to various preferred embodiments of the present invention, it is possible to provide an activity information measuring apparatus that contributes to health improvement by preventing forgotten attachment thereof, and a method and a program for assisting prevention of forgotten attachment of the same.

While the present invention has been described with reference to a specific preferred embodiments, the present invention is not limited to these preferred embodiments, and many variations and modifications can be made without departing from the technical idea of the present invention.

While preferred embodiments of the present invention have been described above, it is to be understood that variations and modifications will be apparent to those skilled in the art without departing from the scope and spirit of the present invention. The scope of the present invention, therefore, is to be determined solely by the following claims.

What is claimed is:

1. An activity information measuring apparatus that is attached to a user for use, the activity information measuring apparatus comprising:
    a detector that detects information corresponding to motion of the user;
    a sleeping state determiner that determines whether or not the user is in a sleeping state;
    a timing detector that, based on the information detected by the detector, determines a timing at which the user has woken from the sleeping state and started to move after the sleeping state determiner determined that the user is in the sleeping state; and an announcer that makes an announcement to the user by sound, light, or vibration in synchronization with the timing.

2. The activity information measuring apparatus according to claim 1, wherein
the sleeping state determiner determines whether or not the user is in the sleeping state based on information detected by the detector; and
the timing detector determines that the user has woken from the sleeping state and started to move if an activity level of the user that is based on information detected by the detector changed to a value that is larger than, by an amount greater than or equal to a threshold value, a value in a period for which it was determined that the user is in the sleeping state, and furthermore if the time at which the change occurred is at or after a specified time.

3. The activity information measuring apparatus according to claim 2, further comprising a time determiner that determines the specified time according to a history of times at which the timing was detected by the timing detector.

4. The activity information measuring apparatus according to claim 2,
further comprising a storage that stores data regarding a sleeping period of the user during which it is determined that the user is in the sleeping state; wherein
if the sleeping state determiner cannot determine whether or not the user is in the sleeping state, the timing detector detects, based on information detected by the detector, a timing at which the user moved at or after a past wakeup time that is based on data stored in the storage, and uses the detected timing as the timing at which the user started to move after the sleeping state ended.

5. A method for assisting prevention of forgotten attachment of an activity information measuring apparatus, the method comprising:
a step in which the activity information measuring apparatus, which is attached to a user for use and includes a detector that detects information corresponding to motion of the user, detects whether or not the user is in a sleeping state;
a step in which the activity information measuring apparatus detects, based on the information detected by the detector, a timing at which the user has woken from the sleeping state and started to move after detection that the user is in the sleeping state; and
a step in which the activity information measuring apparatus makes an announcement to the user by sound, light, or vibration in synchronization with the detected timing.

6. A non-transitory computer-readable medium including a program to assist prevention of forgotten attachment and that causes a computer to execute the steps of the method of claim 5.

* * * * *